US00PP10255P

United States Patent [19]

Neeman

[11] Patent Number: Plant 10,255

[45] Date of Patent: Feb. 24, 1998

[54] NEW GUINEA IMPATIENS PLANT NAMED 'VOLCANO LIGHT PINK'

[75] Inventor: Lior Neeman, D.N. Emek Sorek, Israel

[73] Assignee: Milestone Agriculture Inc., Apopka, Fla.

[21] Appl. No.: 699,602

[22] Filed: Apr. 19, 1996

[51] Int. Cl.[6] ..... A01H 5/00

[52] U.S. Cl. ..... Plt./87.6

[58] Field of Search ..... Plt./87.6

*Primary Examiner*—James R. Feyrer

*Attorney, Agent, or Firm*—C. A. Whealy

[57] ABSTRACT

A new and distinct cultivar of New Guinea Impatiens plant named 'Volcano Light Pink', characterized by its light pink flowers with red star and red purple eye; moderate vigor; dark green, glossy, non-variegated foliage; and freely branching plant habit.

1 Drawing Sheet

The present invention relates to a new and distinct cultivar of New Guinea Impatiens plant, botanically known as *Impatiens hawkeri*, and hereinafter referred to by the cultivar name Volcano Light Pink.

The new cultivar is a product of a planned breeding program conducted by the inventor in Paraiso, Costa Rica. The objective of the breeding program was to develop new varieties that are freely branching, uniform in plant habit, and have bright flower colors.

The new cultivar originated from a cross made by the inventor in January, 1994, of two unnamed proprietary seedlings. The cultivar Volcano Light Pink was discovered and selected by the inventor as a flowering plant within the progeny of the stated cross in a controlled environment in Paraiso, Costa Rica. Asexual reproduction of the new cultivar by terminal cuttings taken at Paraiso, Costa Rica, has shown that the unique features of this new Impatiens are stable and reproduced true to type in successive generations of asexual reproduction.

The following traits have been repeatedly observed and are determined to be the unique characteristics of 'Volcano Light Pink'. These characteristics in combination distinguish 'Volcano Light Pink' as a new and distinct cultivar:

1. Light pink flowers with a faint red star and red purple eye.
2. Moderate vigor.
3. Dark green, glossy, non-variegated foliage.
4. Freely branching plant habit.

The new Impatiens is similar in flower color to the cultivar Danlight, disclosed in U.S. Plant Pat. No. 8,276. However in side-by-side comparisons conducted in Apopka, Florida, plants of the new Impatiens were more compact in growth habit and had a softer flower color than plants of the cultivar Danlight. The new Impatiens is also similar to the cultivar Pago Pago, disclosed in U.S. Plant Pat. No. 9,143. However in side-by-side comparisons conducted in Apopka, Florida, plants of the new Impatiens had a more uniform plant habit, shinier leaves and softer flower color than plants of the cultivar Pago Pago.

The accompanying colored photograph illustrates the overall appearance of the new cultivar, showing the colors as true as it is reasonably possible to obtain in colored reproductions of this type. The photograph comprises a top perspective view of a typical plant of 'Volcano Light Pink'. The flower and foliage colors in the photographs may appear lighter than the actual colors due to light reflectance.

The cultivar Volcano Light Pink has not been observed under all possible environmental conditions. The phenotype may vary somewhat with variations in environment such as temperature and light intensity, without, however, any variance in genotype. The following observations, measurements and comparisons describe plants grown in Apopka, Florida, under commercial practice in a polyethylene-covered greenhouse in 25-cm containers with five plants per container.

In the following description, color references are made to The Royal Horticultural Society Colour Chart except where general terms of ordinary dictionary significance are used.

Classification:

*Botanical.*—*Impatiens hawkeri.*

*Commercial.*—New Guinea Impatiens.

*Cultivar.*—Volcano Light Pink.

Parentage:

*Male parent.*—Unnamed proprietary seedling.

*Female parent.*—Unnamed proprietary seedling.

Propagation:

*Type cutting.*—Type cuttings.

*Time to initiate roots.*—About 7 days with 21° C. soil temperature.

Plant description:

*General appearance.*—Rounded and dense plant form; freely branching; upright and uniform growth habit; moderate vigor.

*Plant height.*—About 27 cm from soil level to top of plant plane.

*Foliage description.*—Shape: Elliptic with acuminate tip and attenuate base. Size: Length: About 10 cm. Width: About 4 cm. Texture: Smooth, glossy, and glabrous. Margin: Finely serrated, ciliate. Petiole length: About 3 cm. Color: Young foliage, upper surface: Darker than 147A. Young foliage, lower surface: 183C, green overtones. Mature foliage, upper surface: Darker than 147A. Mature foliage, lower surface: 183B. Veins, upper surface: 59A. Veins, lower surface: 59A. Petiole: 59A. *Stem description.*—*Internode length: About* 5 cm. Stem color: Mature: 144A. Immature: 59A.

Flower Description:

*Flowering habit.*—Freely flowering.

*Natural flowering season.*—Year-round. Plants usually flower 7 to 8 weeks after planting.

*Flowers borne.*—Flower buds develop in apical leaf axils. Open flowers are displayed above the foliage.

*Quantity of flowers.*—Usually 8 to 10 flower buds and open flowers per terminal.

*Flower longevity on plant.*—From opening, flowers last about 7 days.

*Flower height.*—About 5 cm.

*Flower width.*—About 5 cm.

*Flower depth.*—About 6 mm.

*Petals.*—Shape: Cordate. Quantity, arrangement: 5 petals overlapping. Aspect: Cupped. Size: Length: Uppermost petal: About 2.2 cm. Lower petals: About 2.8 cm. Width: Uppermost petal: About 3 cm. Lower petals: About 2.5 cm. Texture: Smooth, satiny, and glabrous. Margin: Entire. Color: Upper surface: Iridescent; light pink background of 56B; midveins of 50B forming a faint red star; reddish midvein on uppermost petal most prominent margins, 50B; red purple base of 57A forming a red purple eye. Lower surface: Iridescent; light pink background of 55D; midveins of 50B forming a faint red star; red purple base of 57A.

*Peduncle..*—Angle: Erect. Length: About 4 cm. Color: 145A.

*Flower bud.*—Shape: Ovoid with spur. Length: About 1.5 cm. Diameter: About 1 cm. Color: Upper surface: 53A. Lateral and lower surfaces: 50A.

*Spur.*—Shape: Needle-shaped, curved at end. Color: Flower bud: 145A. Opened flower: 145C.

*Sepals.*—Arrangement: Opposite. Quantity: 2. Shape: Ensiform with acuminate tip. Texture: Shiny, smooth and glabrous. Margin: Entire. Color: Upper side: 50A. Lower side: Light green with red overtones.

*Reproductive organs.*—Androecium: Quantity of stamens: 5. Anther color: Creamy white. Pollen color: 11D. Gynoecium: Ovary color: 59A.

Disease Resistance: Under commercial conditions, no fungal, bacterial nor viral problems observed.

Seed development: Seed production is not usually observed.

It is claimed:

1. A new and distinct cultivar of New Guinea Impatiens plant named 'Volcano Light Pink', as illustrated and described.

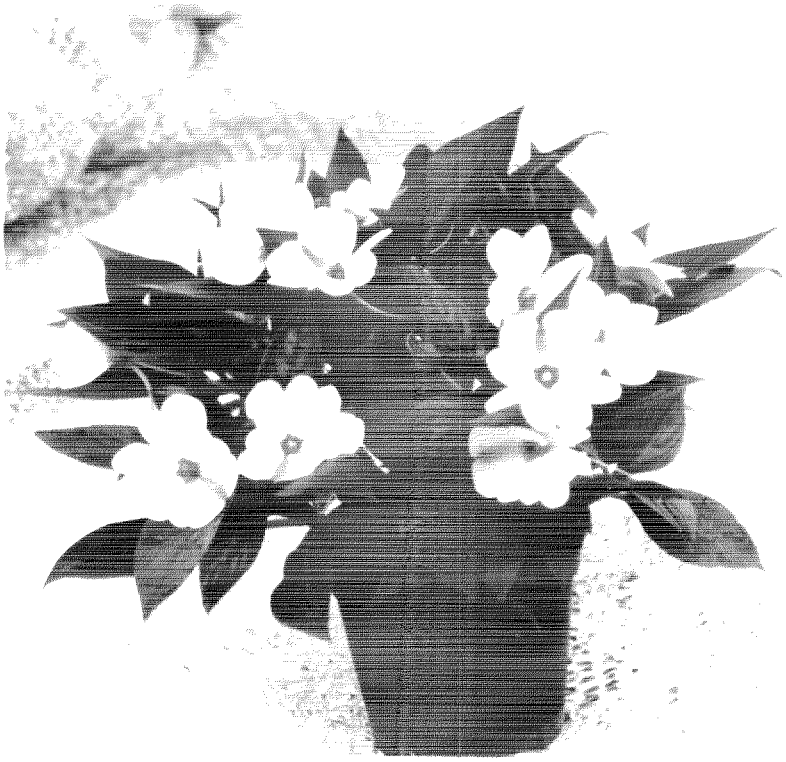

* * * * *